United States Patent [19]

Stein

[11] Patent Number: Plant 7,227

[45] Date of Patent: May 8, 1990

[54] APPLE 'TOMER'

[75] Inventor: Abba Stein, Ein Shemer, Israel

[73] Assignee: Fruit Board, Tel-Aviv, Israel

[21] Appl. No.: 219,060

[22] Filed: Jun. 29, 1988

[51] Int. Cl.[5] ..... A01H 5/00

[52] U.S. Cl. ..... Plt./34

[58] Field of Search ..... Plt./34

*Primary Examiner*—James R. Feyrer

*Attorney, Agent, or Firm*—Browdy and Neimark

[57] ABSTRACT

An apple variety derived by hybridization from Red Delicious×Anna $F_2$ is distinguished by the fact that it can be grown successfully without the necessity for an extreme degree of cold in the winter season.

2 Drawing Sheets

This invention relates to new and distinct variety of the apple *Malus sylvestris L.*

The new apple was produced by hybridization from Red Delicious×Anna $F_2$. Propagation is by asexual reproduction (grafting of cuttings). The new variety has been grown and examined over a period of seven years at Ein Shemer and Kvutzat Shilar, Israel. In Israel, the variety is grown in irrigated fields. The new variety has been tested for a period of two years the Ministry of Agriculture, Plant Breeders' Rights Council, Bet Dagan, Israel. The fruit of the new variety is generally medium firm to firm, has red cheeks, is conical in shape and is slightly tart/slightly sweet; the size is medium to large. In Israel, the new variety flowers at the end of February to the beginning of March, and the apples are harvested generally at the end of July, or possibly from the middle of July. In appearance, the fruit of the new variety resembles the "Anna" apple, but ripens later. The apple of the new invention is suitable for eating in the fresh state.

DESCRIPTION OF THE TREE, SHOOTS AND FLOWERS

Figure 1:
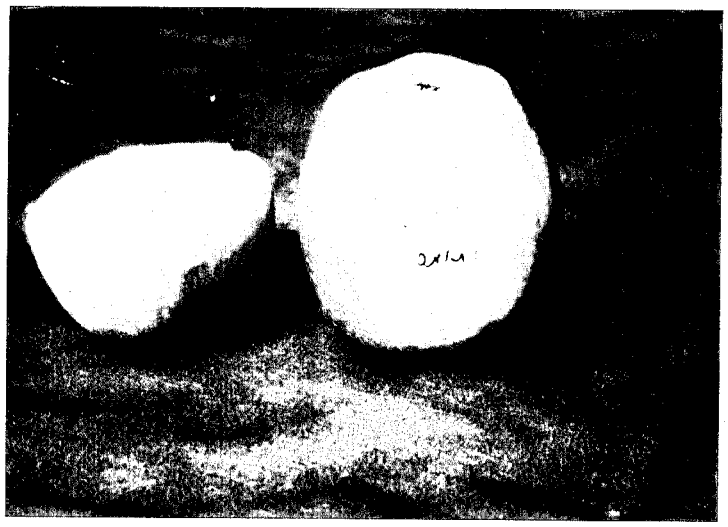
FIG. 1 is a photograph of respective whole and cut samples of ripe apples of the variety described, the locules of the fruit being clearly visible in the cut sample.
Figure 2:
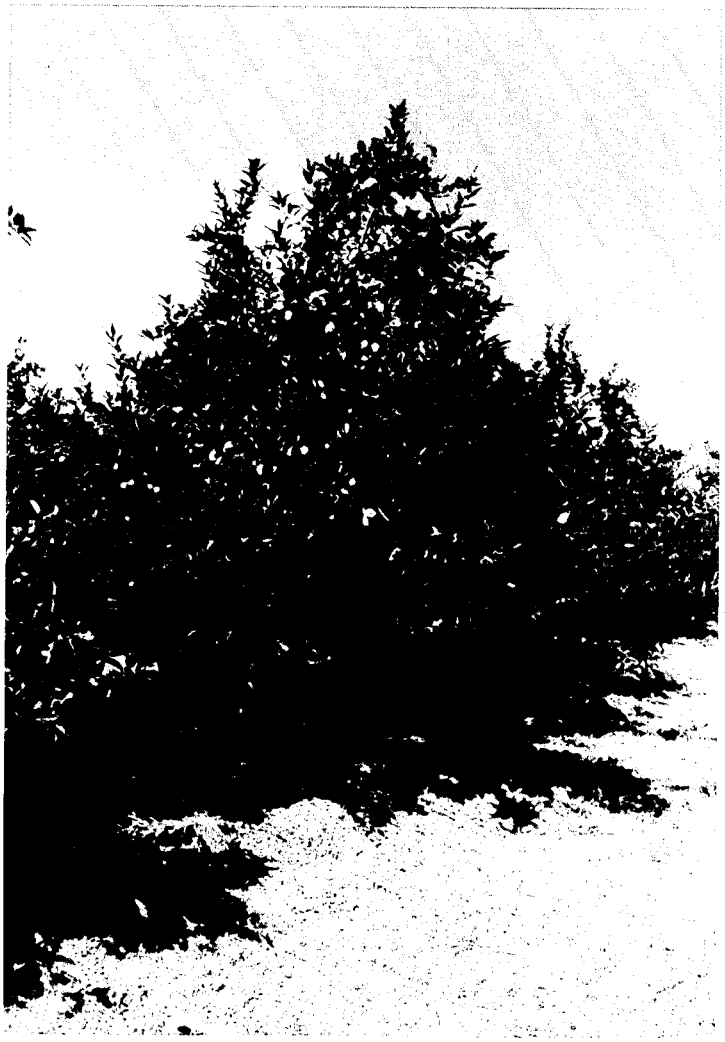
FIG. 2 is a photograph of a seven year old tree in full foliage prior to picking time.
Figure 3:
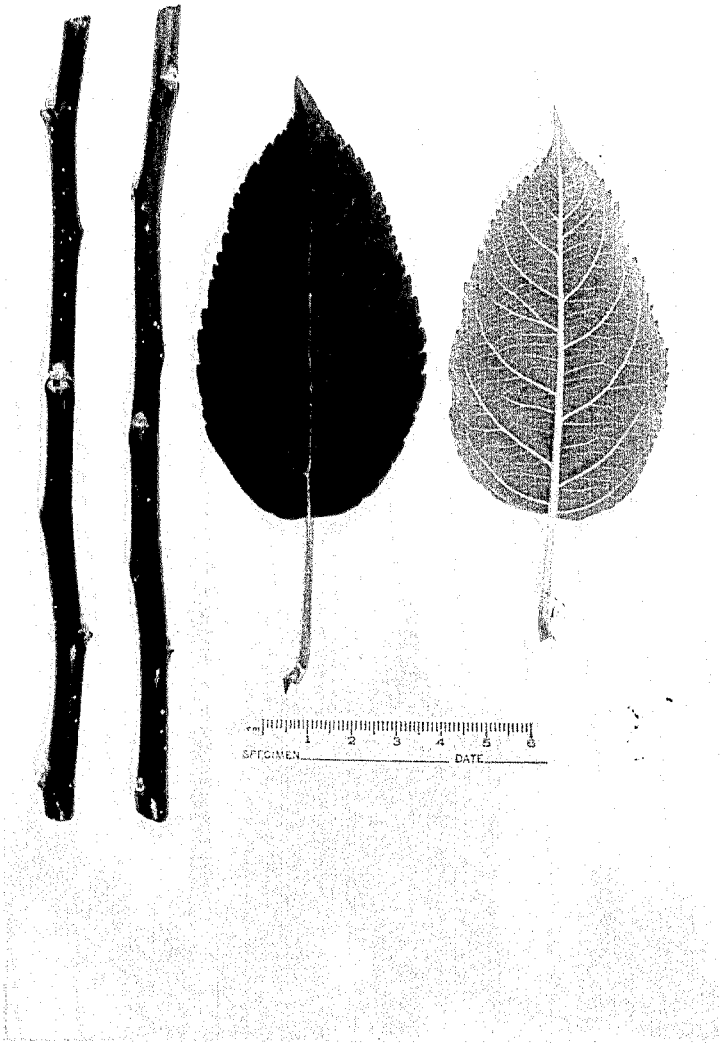
FIG. 3 is a photograph of twigs and leaves of the new variety. The one year old shoots are shown to have small-sized scattered lenticles and adpressed buds having small-pointed tips. The lower side of the leaf (on the right side of the photograph) has very weak anthocyanin coloration of the veins. The upper side of the leaf (in the middle of the photograph) is a dark green color.

The tree is of spreading habit, ultimately 5 m high and 5 to 5.5 m wide (on *Malus communis* rootstock) with medium density of branches, the growth is vigorous and the growth of the shoots is wavy and fruit is borne predominantly on shoots. The characteristics of a one year old shoot are as follows: weak pubescence on upper half, medium shine on the bark, thickness (diameter at center) about 6 mm., strong flexibility, 8 nodes per 20 cm., many small size lenticels, predominant color on the sunny side—brown (RHS-177A), small bud with pointed tip, position of bud relative to axis—adpressed, small bud support and strong crimping thereof. The flower bud is dark pink before the flower opens, the pedicel is red. The medium size single flower has ovate petals, the petal margins are overlapping, the color of the petal upper side is 55CD and 55D when faded (RHS Colour Chart). The productivity is as "Delicious" and the pollination is as with varieties "Anna" and "Ein Shemer" in the coastal plain in Israel. Thinning of branches and of fruit is required.

DESCRIPTION OF THE LEAF

The leaf is of medium to large size, between concave and straight in cross-section, shape of the apex mucronate. The leaf blade, which is colored green (RHS-135A) when expanding, shows serrate indentation of margin, weak glossiness of the upper side, strong pubescence on the lower side and very weak anthocyanin coloration of the veins. The upper side, from which anthocyanin coloration is absent, is dark green (RHS-135A).

FRUIT CHARACTERISTICS

The fruit size is classified as medium to large. The shape is conical, and asymmetric in side view. Ribbing is absent or very weak. There is a strong degree of crowning at the distal end. The eye is closed and is of medium size; there is a deep and broad basin at the eye end of the fruit. Persistence of the calyx is present. The medium size sepals overlap at the base. The fruit stalk is short and thin; the stalk cavity is of medium depth, but is narrow. The fruit has a smooth surface, skin bloom is present; greasiness, translucency and any cracking tendency of the skin are all absent. The skin is thin, its ground color is yellow (RHS-11P), it has a medium amount of orange red over color, this being of solid flush type. The amount of russet, which is found around the eye basin, is very low. The lenticels are of medium size. The flesh is medium firm to firm, juicy, greenish in color and has a fine texture; grittiness is absent. Any browning of the flesh one hour after being cut with a stainless steel knife is either absent or very weak. The fruit in cross section shows either no or very weak distinctiveness of the core and closed aperture of locules. The fruit has 5 locules and typically 5 to 10 seeds, the shape of which is elongated. Both the time of picking for commercial harvest and the time of fruit ripening for eating are (in Israel) generally at the end of July. The keeping quality of the fruit is medium. The fruit can be kept on the tree until full ripening.

Response of the tree to drought—full irrigation is required; the tree has no special resistance to insects or to diseases. The degree of salt tolerance is dependent on the type of rootstock.

We have designated the new variety "Tomer". The "Tomer" variety possesses the advantage that it can be grown successfully without the necessity of the extreme degree of cold in the winter season, as has usually been necessary hitherto. This means of course that the apple has the potential for being grown in climates with winters which are relatively milder than climates in which apples are usually grown.

I claim:

1. The new and distinct variety of eating apple substantially as described and illustrated herein, being derived by hybridization from Red Delicious × Anna $F_2$ and distinguished by the fact that it can be grown successfully without the necessity for an extreme degree of cold in the winter season.

* * * * *